(12) United States Patent
Mitsuoka et al.

(10) Patent No.: US 10,662,134 B2
(45) Date of Patent: May 26, 2020

(54) SOLVENT COMPOSITION, CLEANING METHOD, COATING FILM-FORMING COMPOSITION, AND METHOD OF FORMING A COATING FILM

(71) Applicant: AGC Inc., Chiyoda-ku (JP)

(72) Inventors: Hiroaki Mitsuoka, Chiyoda-ku (JP); Daisuke Ikeda, Chiyoda-ku (JP); Toshio Miki, Chiyoda-ku (JP); Tsuyoshi Hanada, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 117 days.

(21) Appl. No.: 16/047,847

(22) Filed: Jul. 27, 2018

(65) Prior Publication Data

US 2018/0370882 A1   Dec. 27, 2018

Related U.S. Application Data

(63) Continuation of application No. PCT/JP2017/002783, filed on Jan. 26, 2017.

(30) Foreign Application Priority Data

Jan. 29, 2016   (JP) ................................. 2016-015500

(51) Int. Cl.
  *C07C 21/073*   (2006.01)
  *C07C 23/10*   (2006.01)
  (Continued)

(52) U.S. Cl.
  CPC ............. *C07C 21/073* (2013.01); *B08B 3/08* (2013.01); *C07C 19/08* (2013.01); *C07C 23/10* (2013.01);
  (Continued)

(58) Field of Classification Search
  CPC ........ C07C 21/073; C07C 19/08; C07C 23/10
  See application file for complete search history.

(56) References Cited

U.S. PATENT DOCUMENTS 7,053,035 B2 *   5/2006   Hanada ................ C11D 7/5018
                                                                510/177
8,748,363 B2 *   6/2014   Nagashima ............ G21F 9/002
                                                                134/22.19
(Continued)

FOREIGN PATENT DOCUMENTS

AU   2002349452 A1   6/2003
AU   2003281307 A1   1/2004
(Continued)

OTHER PUBLICATIONS

International Search Report dated Mar. 21, 2017 in PCT/JP2017/002783, filed on Jan. 26, 2017 (with English Translation).

*Primary Examiner* — Liam J Heincer
*Assistant Examiner* — M. Reza Asdjodi
(74) *Attorney, Agent, or Firm* — Oblon, McClelland, Maier & Neustadt, L.L.P.

(57) ABSTRACT

There are provided a solvent composition containing tDCE, which does not exert an adverse effect on the global environment, has high solubility and incombustibility, and can maintain initial incombustibility even in use accompanied by a phase change, a cleaning method using the solvent composition, a coating film-forming composition including the solvent composition, and a method of forming a homogeneous coating film using the coating film-forming composition. A solvent composition includes: tDCE; at least one HFE (A) selected from HFE-347pc-f, HFE-365mf-c, and HFE-467sc-f; and at least one HFC (X) selected from cHFC-447, and HFC-76-13sf, in which a ratio of tDCE with respect to a total amount of tDCE, HFE (A), and HFC (X) is 65 to 80 mass %, a ratio of HFE (A) with respect to the (Continued)

total amount is 5 to 25 mass %, and a ratio of HFC (X) with respect to the total amount is 5 to 25 mass %.

11 Claims, 1 Drawing Sheet

(51) Int. Cl.

| | | |
|---|---|---|
| C07C 19/08 | (2006.01) | |
| C11D 7/30 | (2006.01) | |
| C23G 5/028 | (2006.01) | |
| C09D 7/40 | (2018.01) | |
| C11D 7/50 | (2006.01) | |
| C11D 7/26 | (2006.01) | |
| C10M 107/38 | (2006.01) | |
| C11D 11/00 | (2006.01) | |
| B08B 3/08 | (2006.01) | |
| C09D 201/00 | (2006.01) | |
| C10M 107/50 | (2006.01) | |
| C09D 7/20 | (2018.01) | |
| C09D 7/63 | (2018.01) | |
| C07C 43/12 | (2006.01) | |

(52) U.S. Cl.
CPC ............. *C07C 43/123* (2013.01); *C09D 7/20* (2018.01); *C09D 7/40* (2018.01); *C09D 7/63* (2018.01); *C09D 201/00* (2013.01); *C10M 107/38* (2013.01); *C10M 107/50* (2013.01); *C11D 7/263* (2013.01); *C11D 7/30* (2013.01); *C11D 7/50* (2013.01); *C11D 7/5018* (2013.01); *C11D 11/00* (2013.01); *C11D 11/0047* (2013.01); *C23G 5/028* (2013.01); *C23G 5/02806* (2013.01); *C10M 2213/0606* (2013.01); *C10M 2229/025* (2013.01); *C10N 2220/12* (2013.01); *C10N 2220/13* (2013.01); *C10N 2230/22* (2013.01); *C10N 2240/06* (2013.01); *C10N 2240/20* (2013.01); *C10N 2240/401* (2013.01); *C10N 2250/121* (2013.01)

(56) References Cited

U.S. PATENT DOCUMENTS

| | | |
|---|---|---|
| 2005/0109988 A1 | 5/2005 | Hanada et al. |
| 2008/0139444 A1 | 6/2008 | Bartelt |
| 2010/0108094 A1* | 5/2010 | Ishikawa ................. G21F 9/002 134/6 |
| 2013/0072409 A1* | 3/2013 | Ishikawa ................. G21F 9/002 510/110 |
| 2015/0037505 A1 | 2/2015 | Tsuzaki et al. |
| 2015/0315531 A1 | 11/2015 | Uenveren et al. |
| 2018/0370882 A1* | 12/2018 | Mitsuoka ................. C11D 7/30 |

FOREIGN PATENT DOCUMENTS

| | | |
|---|---|---|
| CA | 2 491 467 A1 | 1/2004 |
| CN | 1665917 A | 9/2005 |
| CN | 101553561 A | 10/2009 |
| CN | 104245907 A | 12/2014 |
| DE | 11 2013 002 166 T5 | 1/2015 |
| EP | 2 336 288 A1 | 6/2011 |
| EP | 2 876 153 A1 | 5/2015 |
| JP | 10-324652 | 12/1998 |
| JP | 2879847 | 4/1999 |
| JP | 2001-32091 | 2/2001 |
| JP | 2005-48097 | 2/2005 |
| JP | 2010-512448 | 4/2010 |
| JP | 4556669 | 10/2010 |
| JP | 2013-224383 | 10/2013 |
| JP | 5618540 | 11/2014 |
| KR | 10-1002202 | 2/2005 |
| TW | 200900501 | 1/2009 |
| TW | 200402411 | 9/2010 |
| TW | 201437348 A | 10/2014 |
| WO | WO 03/044148 A1 | 5/2003 |
| WO | WO 2004/005445 A1 | 1/2004 |
| WO | WO 2008/073408 A1 | 6/2008 |
| WO | WO 2013/161723 A1 | 10/2013 |
| WO | WO 2014/139865 A1 | 9/2014 |

* cited by examiner

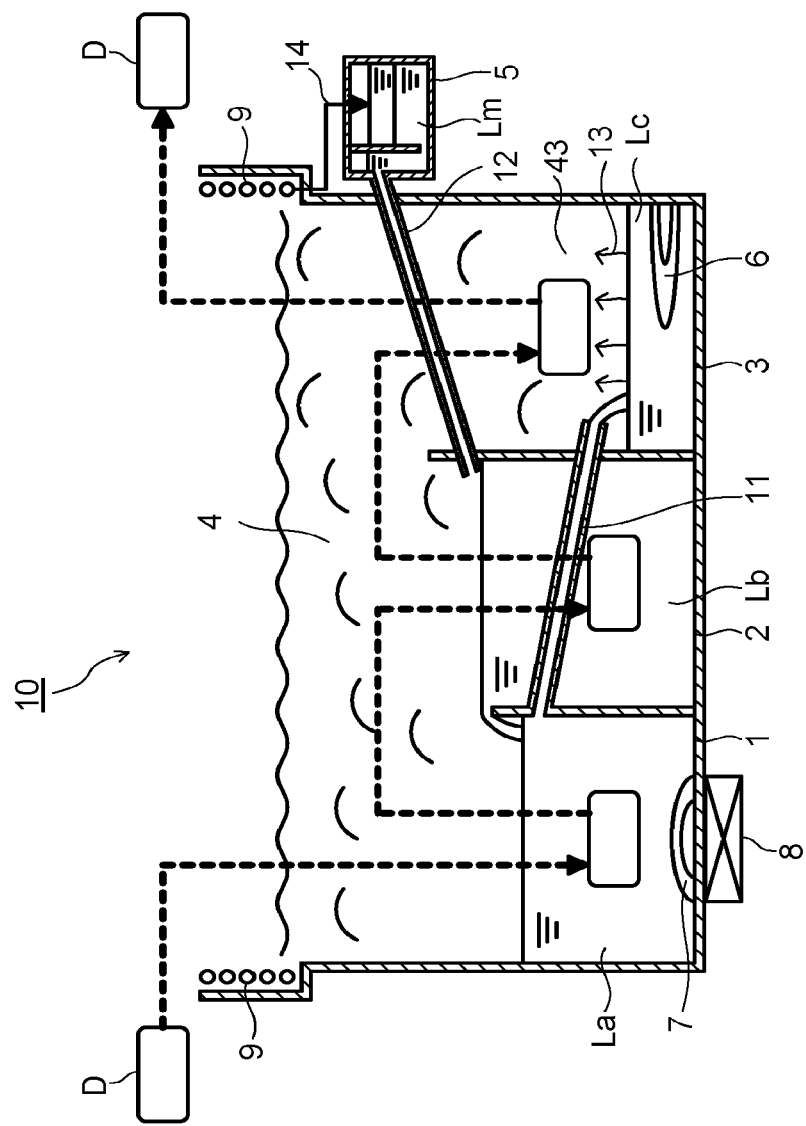

SOLVENT COMPOSITION, CLEANING METHOD, COATING FILM-FORMING COMPOSITION, AND METHOD OF FORMING A COATING FILM

CROSS-REFERENCE TO RELATED APPLICATIONS

This application is a continuation of prior International Application No. PCT/JP2017/002783, filed on Jan. 26, 2017 which is based upon and claims the benefit of priority from Japanese Patent Application No. 2016-015500, filed on Jan. 29, 2016; the entire contents of all of which are incorporated herein by reference.

TECHNICAL FIELD

The present invention relates to a solvent composition, a cleaning method using the solvent composition, a coating film-forming composition using the solvent composition as a dilution coating solvent, and a method of forming a coating film using the coating film-forming composition.

BACKGROUND

Conventionally, when manufacturing ICs, electronic components, precision machinery components, optical components, and the like, precision cleaning of components has been widely performed by using a fluorine-based solvent in order to remove flux, a machining oil, wax, a release agent, dust, and the like adhering to the components. Further, in a method in which a composition obtained by dissolving various coating film forming components such as a lubricant in a solvent is applied on a surface of an article, and then the solvent is evaporated to form a coating film, it has been known to use a fluorine-based solvent as the solvent.

As the above-described fluorine-based solvent, chlorofluorocarbon (hereinafter, referred to as "CFC"), hydrochlorofluorocarbon (hereinafter, referred to as "HCFC"), and so on are used because they have high solubility with respect to nonvolatile compounds such as a machining oil and a lubricant, have incombustibility and low toxicity, have excellent stability, do not encroach on a base material of metal, plastic, elastomer, or the like, and have excellent chemical and thermal stability.

However, because CFC and HCFC are chemically quite stable, they each have a long lifetime in the troposphere after vaporization, and diffuse and reach the stratosphere. For this reason, there is a problem that CFC or HCFC reached the stratosphere is decomposed by ultraviolet rays to generate chlorine radicals, which deplete an ozone layer.

As a solvent which does not exert an adverse effect on the ozone layer, perfluorocarbon (hereinafter, referred to as "PFC"), hydrofluorocarbon (hereinafter, referred to as HFC), hydrofluoroether (hereinafter, referred to as HFE), and the like are known. However, because HFC and PFC have a large global warming potential, they are regulation object substances in the Kyoto Protocol. Further, HFC, HFE, and PFC have problems in that they have low solubility of the nonvolatile compounds.

As a solvent which does not exert an adverse effect on the global environment, has low toxicity, and has excellent solubility of the nonvolatile compounds, trans-1,2-dichloroethylene (trans-CHCl=CHCl, which is also referred to as "tDCE", hereinafter) is known. However, tDCE has an inflammation point, so that it is difficult to be used alone.

Accordingly, it has been proposed to prepare an azeotropic or azeotropic-like composition by combining tDCE and HFE having no inflammation point, and use this composition for cleaning and the like as an incombustible solvent composition. For example, Patent Reference 1 (JP-B No. 2879847) describes an azeotropic or azeotropic-like composition consisting of tDCE and 1,1,2,2-tetrafluoroethyl-2,2,2-trifluoroethyl ether ($CF_3CH_2OCF_2CF_2H$, which is also referred to as "HFE-347pc-f", hereinafter). Further, Patent Reference 2 (JP-B No. 4556669) describes a solvent composition containing an azeotropic or azeotropic-like composition consisting of tDCE, HFE-347pc-f, and methanol, ethanol or 2-propanol.

SUMMARY OF THE INVENTION

The solvent composition described in each of Patent Reference 1 and Patent Reference 2 is the azeotropic-like composition, so that even if it is used in a solvent cleaning apparatus in which evaporation and condensation are repeated, there is no chance that a concentration of tDCE changes in accordance with a phase change, so that the solvent composition can be used safely while maintaining incombustibility. However, as a result of adjusting the composition to realize the azeotropic-like composition, a content of tDCE is 40 to 50 mass % in the composition in Patent Reference 1, and a content of tDCE is 61 mass % at maximum in the composition in Patent Reference 2, and as above, it is not possible to increase the contents of tDCE to contents equal to or greater than the above contents. As described above, when compared to tDCE, HFE has low solubility with respect to the nonvolatile compounds such as the machining oil and the lubricant, and accordingly, it is not possible to obtain sufficiently high solubility in the solvent compositions described in Patent Reference 1 and Patent Reference 2.

Further, if tDCE is contained in a high concentration in order to obtain high solubility with respect to the nonvolatile compounds such as the machining oil and the lubricant, the incombustibility of the solvent composition cannot be maintained since tDCE has an inflammation point.

The present invention has been made to solve the above-described problems, and an object thereof is to provide a solvent composition containing tDCE, which does not exert an adverse effect on the global environment, has high solubility and incombustibility, and can maintain initial incombustibility even in use accompanied by a phase change, and a cleaning method of an article using the solvent composition, the cleaning method having high cleaning performance, exerting no adverse effect on the global environment, and having secured safety.

Further, the present invention has an object to provide a coating film-forming composition which uses a solvent composition containing tDCE, whose volatile component does not exert an adverse effect on the global environment when used, which has incombustibility, and which can form a homogeneous coating film, and a method of forming a homogeneous coating film by using the coating film-forming composition, in a safe manner without exerting an adverse effect on the global environment.

The present invention provides a solvent composition, a cleaning method, a coating film-forming composition, and a method of forming a coating film which have the following configurations.

[1] A solvent composition including: trans-1,2-dichloroethylene (which is also referred to as "tDCE", hereinafter); at least one hydrofluoroether (A) (which is also referred to as HFE (A), hereinafter) selected from a group consisting of 1,1-difluoroethyl-2,2,2-trifluoroethyl ether (which is also referred to as "HFE-365mf-c", hereinafter), 1,1,2,2-tetrafluoroethyl-2,2,2-trifluoroethyl ether (which is also referred to as "HFE-347pc-f", hereinafter), and 1,1-difluoroethyl-2,2,3,3,3-pentafluoropropyl ether (which is also referred to as "HFE-467sc-f", hereinafter); and at least one hydrofluorocarbon (X) (which is also referred to as HFC (X), hereinafter) selected from a group consisting of 1,1,2,2,3,3,4-heptafluorocyclopentane (which is also referred to as "cHFC-447", hereinafter), and 1,1,1,2,2,3,3,4,4,5,5,6,6-tridecafluorohexane (which is also referred to as "HFC-76-13sf", hereinafter), wherein a ratio of tDCE with respect to a total amount of tDCE, the HFE (A), and the HFC (X) is 65 to 80 mass %, a ratio of the HFE (A) with respect to the total amount is 5 to 25 mass %, and a ratio of the HFC (X) with respect to the total amount is 5 to 25 mass %.

[2] The solvent composition according to [1], wherein a ratio of tDCE with respect to a total amount of tDCE and the HFE (A) is 75 to 90 mass %.

[3] The solvent composition according to [1], wherein a ratio of the total amount of tDCE, the HFE (A), and the HFC (X) with respect to a total amount of the solvent composition is 90 to 100 mass %.

[4] The solvent composition according to [1], wherein the HFE (A) is HFE-347pc-f.

[5] The solvent composition according to [1], wherein the HFC (X) is cHFC-447.

[6] The solvent composition according to [1], used for cleaning stain of an article to be cleaned.

[7] A cleaning method including: bringing the solvent composition according to [6] and an article to be cleaned into contact with each other.

[8] A coating film-forming composition including: the solvent composition according to [1]; and a nonvolatile organic compound.

[9] The coating film-forming composition according to [8], wherein the nonvolatile organic compound is a lubricant.

[10] The coating film-forming composition according to [9], wherein the lubricant is at least one selected from a silicone-based lubricant and a fluorine-based lubricant.

[11] A method of forming a coating film including: applying the coating film-forming composition according to [8] on an article to be coated; and then evaporating the solvent composition to form a coating film consisting of the nonvolatile organic compound.

A solvent composition of the present invention does not exert an adverse effect on the global environment, has incombustibility and high solubility, and can maintain initial incombustibility even in use accompanied by a phase change.

A cleaning method of the present invention can clean an article with high cleaning performance and high safety without exerting an adverse effect on the global environment. A coating film-forming composition of the present invention is excellent in solubility of a nonvolatile organic compound, can form a homogeneous coating film on a surface of an article to be coated, exerts no adverse effect on the global environment even if it is volatilized, and has incombustibility.

A method of forming a coating film of the present invention enables to form a homogeneous coating film on a surface of an article to be coated safely without exerting an adverse effect on the global environment.

BRIEF DESCRIPTION OF THE DRAWINGS

[FIG. 1] is a view schematically illustrating one example of a cleaning apparatus carrying out a cleaning method of the present invention.

MODES FOR CARRYING OUT THE INVENTION

[Solvent Composition]

A solvent composition of the present invention contains tDCE, at least one HFE (A) selected from a group consisting of HFE-365mf-c, HFE-347pc-f, and HFE-467sc-f, and at least one HFC (X) selected from a group consisting of cHFC-447, and HFC-76-13sf, in which a ratio of tDCE with respect to a total amount of tDCE, HFE (A), and HFC (X) is 65 to 80 mass %, a ratio of HFE (A) with respect to the total amount is 5 to 25 mass %, and a ratio of HFC (X) with respect to the total amount is 5 to 25 mass %.

In the present invention, when tDCE, HFE (A), and HFC (X) are combined to have the above ratios, respectively, to be used, it becomes possible to provide a composition having incombustibility while it is a composition having a high content of tDCE and high solubility, and maintaining incombustibility by making a tDCE concentration in a gas phase and a tDCE concentration in a liquid phase to be nearly equal even in use accompanied by a phase change. Hereinafter, respective components contained in the solvent composition of the present invention will be described.

(tDCE)

tDCE is an olefin having a double bond between a carbon atom and a carbon atom, so that its lifetime in the atmosphere is short, and does not exert an adverse effect on the global environment. tDCE has a boiling point of about 49° C., and thus is excellent in a drying property. Further, even if it is boiled to turn into steam, a temperature thereof is about 49° C., so that it is difficult to exert an adverse effect even on parts susceptible to heat. tDCE has low surface tension and viscosity, and easily evaporates even at room temperature.

tDCE has chlorine in a molecule, so that its solubility with respect to an organic matter such as a machining oil is quite high, and thus it can be used for degreasing cleaning of the machining oil, flux cleaning, precision cleaning, and the like. tDCE is excellent in solubility of a nonvolatile organic compound such as a lubricant. Therefore, tDCE can be used as a solvent of a coating film-forming solution or the like in which the nonvolatile organic compound is used as a solute. Meanwhile, tDCE has an inflammation point.

In the present specification, having an inflammation point means having an inflammation point from 23° C. to a boiling point, and having no inflammation point means having no inflammation point from 23° C. to the boiling point. Further, having incombustibility means having no inflammation point.

As a commercially available product of tDCE, the following can be cited, for example.

"Trans-LC (registered trademark)" (manufactured by Daido Air Products Electronics Inc.) "trans-1,2-dichloroethylene" (manufactured by AXIALL CORPORATION)

(HFE (A))

HFE (A) is at least one selected from a group consisting of HFE-365mf-c, HFE-347pc-f, and HFE-467sc-f. As HFE (A), only one kind may be used, or two kinds or more may be combined to be used.

HFE (A) is hydrofluoroether whose boiling point is in a range of 40 to 65° C., and when such HFE (A) is contained in the aforementioned ratio, the solvent composition of the present invention is difficult to cause a change in the concentration of tDCE when it is used in a cleaning apparatus. Further, from a point that the concentration of tDCE is more difficult to be changed, the boiling point of HFE (A) is more preferably 50 to 60° C., and still more preferably 54 to 58° C. From the above-described viewpoint, HFE-347pc-f is the most preferable as HFE (A).

(HFE-347pc-f)

HFE-347pc-f has zero ozone depletion potential, and a small global warming potential. HFE-347pc-f has a boiling point of about 56° C., so that it is excellent in a drying property and it easily evaporates even at room temperature. Further, even if it is boiled to turn into steam, it is difficult to exert an adverse effect on parts susceptible to heat such as resin parts. HFE-347pc-f has no inflammation point. HFE-347pc-f has low surface tension and viscosity.

Although HFE-347pc-f has low solubility with respect to the nonvolatile organic compound such as the machining oil and the lubricant, it has sufficient property as a solvent for cleaning and a solvent in a coating film such as the lubricant film-forming solution.

HFE-347pc-f can be manufactured through the following method, for example. A method in which 2,2,2-trifluoroethanol and tetrafluoroethylene are reacted in the presence of an aprotic polar solvent and a catalyst (alkali metal alkoxide or alkali metal hydroxide) (refer to International Publication No. 2004/108644).

As a commercially available product of HFE-347pc-f, there can be cited the following, for example.

"ASAHIKLIN (registered trademark) AE-3000" (manufactured by Asahi Glass Co., Ltd.)

(HFE-365mf-c)

HFE-365mf-c has zero ozone depletion potential, and a small global warming potential. HFE-365mf-c has a boiling point of 40° C., so that it is excellent in a drying property and it easily evaporates even at room temperature. Further, even if it is boiled to turn into steam, it is difficult to exert an adverse effect on parts susceptible to heat such as resin parts. HFE-365mf-c has low surface tension and viscosity.

HFE-365mf-c can be manufactured through the following method, for example.

A method in which 2,2,2-trifluoroethanol and vinylidene fluoride are reacted in the presence of an aprotic polar solvent and a catalyst (alkali metal alkoxide or alkali metal hydroxide) (refer to JP-A No. H09-263559).

(HFE-467sc-f)

HFE-467sc-f has zero ozone depletion potential, and a small global warming potential. HFE-467sc-f has a boiling point of 59° C., so that it is excellent in a drying property and it easily evaporates even at room temperature. Further, even if it is boiled to turn into steam, it is difficult to exert an adverse effect on parts susceptible to heat such as resin parts. HFE-467sc-f has low surface tension and viscosity.

HFE-467sc-f can be manufactured through the following method, for example. A method in which 2,2,3,3,3-pentafluoropropanol and vinylidene fluoride are reacted in the presence of an aprotic polar solvent and a catalyst (alkali metal alkoxide or alkali metal hydroxide) (refer to JP-A No. H09-263559).

(HFC (X))

HFC (X) is at least one hydrofluorocarbon selected from cHFC-447 and HFC-76-13sf. HFC (X) may be constituted of cHFC-447 or HFC-76-13sf alone, or it may be a mixture of the both. HFC (X) is preferably constituted of cHFC-447 or HFC-76-13sf alone, and it is more preferably constituted of cHFC-447 alone from a viewpoint that a tDCE concentration difference between a gas phase and a liquid phase during use becomes small.

cHFC-447 has zero ozone depletion potential, and a small global warming potential. cHFC-447 has a boiling point of about 82° C., and has no inflammation point. cHFC-447 can be obtained as a commercially available product of, for example, "ZEORORA-H" (manufactured by Zeon Corporation).

cHFC-447 can be manufactured through a publicly-known method. According to a method in JP-B No. 4423414, it is possible to manufacture cHFC-447 by hydrogenating 1-chloroheptafluorocyclopentene in the presence of a hydrogenation catalyst such as aluminum fluoride supporting noble metal.

HFC-76-13sf is a solvent having a boiling point of 115° C. and having no inflammation point. HFC-76-13sf can be obtained as a commercially available product of "ASAHIKLIN (registered trademark) AC-6000" (manufactured by Asahi Glass Co., Ltd.), for example.

(Composition of Solvent Composition)

A solvent composition of the present invention contains tDCE, at least one HFE (A) selected from HFE-365mf-c, HFE-347pc-f, and HFE-467sc-f, and at least one HFC (X) selected from cHFC-447, and HFC-76-13sf, in which a ratio of tDCE with respect to a total amount of tDCE, HFE (A), and HFC (X) is 65 to 80 mass %, a ratio of HFE (A) with respect to the total amount is 5 to 25 mass %, and a ratio of HFC (X) with respect to the total amount is 5 to 25 mass %.

In the solvent composition of the present invention, if only HFE-347pc-f is used as HFE (A), for example, a ratio of tDCE with respect to the total amount of tDCE, HFE-347pc-f, and HFC (X) is 65 to 80 mass %, a ratio of HFE-347pc-f with respect to the total amount of tDCE, HFE-347pc-f, and HFC (X) is 5 to 25 mass %, and a ratio of HFC (X) with respect to the total amount of tDCE, HFE-347pc-f, and HFC (X) is 5 to 25 mass %.

In the solvent composition of the present invention, HFC (X) constituted of cHFC-447 and/or HFC-76-13sf is contained in addition to tDCE and HFE (A) within the above-described composition range, which solves the problem such that in the conventional composition containing tDCE and HFE (A), the incombustibility cannot be maintained in the use accompanied by the phase change if tDCE is contained in a high concentration.

In a two-component composition containing tDCE and any one kind of compounds of HFE (A), if a content of tDCE exceeds a range of an azeotropic-like composition, tDCE is concentrated in a liquid phase during evaporation, resulting in that even the composition having no inflammability at an initial stage changes to a composition having the inflammability (which is also referred to as "inflammable composition", hereinafter) in the use accompanied by the phase change. Therefore, conventionally, by creating an azeotropic-like composition in which a composition change of the composition does not occur almost at all in accordance with the phase change, the concentration of tDCE to a high degree has been suppressed, but, the content of tDCE has not been high in the azeotropic-like composition containing tDCE and any one kind of the compounds of HFE (A).

On the other hand, the solvent composition of the present invention is a composition in which there is no change almost at all in a tDCE content at least in the gas phase and the liquid phase in the use accompanied by the phase change, while having a tDCE content higher than that in the conventional azeotropic-like composition containing tDCE and any one kind of the compounds of HFE (A). It can be considered that this is because HFC (X) added in a predetermined ratio to tDCE and HFE (A) has an operation to accelerate volatilization of tDCE from the liquid phase to the gas phase so that tDCE does not concentrate in the liquid phase during evaporation, to thereby suppress the change in the content of tDCE. Because of the operation, the solvent composition of the present invention can suppress the change in the content of tDCE in a cleaning apparatus in which evaporation and condensation are repeated, for example, and thus can maintain the incombustibility. Further, also when the solvent composition of the present invention is put in a simple cleaning tank to be used, it is possible to suppress that the composition is turned into the inflammable composition when tDCE is concentrated in the liquid phase in accordance with the volatilization of the solvent composition.

In the solvent composition of the present invention, the ratio of tDCE with respect to the total amount of tDCE, HFE (A), and HFC (X) is 65 to 80 mass %. Hereinafter, "the ratio of tDCE" indicates the ratio of tDCE with respect to the total amount of tDCE, HFE (A), and HFC (X). The same applies to "the ratio of HFE (A)", and "the ratio of HFC (X)".

When the ratio of tDCE is less than 65 mass %, it is not possible to sufficiently obtain solubility with the nonvolatile organic compound, particularly, a mineral oil being a main component of the machining oil, so that the machining oil remains on an article to be cleaned after the cleaning. Further, the machining oil mixed due to the cleaning is not dissolved in the solvent composition, resulting in that the solvent composition becomes cloudy or undergoes two-layer separation. When this solvent composition is repeatedly used to clean an article to be cleaned, this becomes a cause of cleaning failure such that the article to be cleaned is contaminated again. On the other hand, when the ratio of tDCE exceeds 80 mass %, it is highly likely that the solvent composition is turned into the inflammable composition in the use accompanied by the phase change such as application for cleaning or application for dilution coating, and thus it is difficult to maintain the incombustibility.

In the solvent composition of the present invention, the ratio of HFE (A) is 5 to 25 mass %. When the ratio of HFE (A) is less than 5 mass %, in the use of the solvent composition accompanied by the phase change, the incombustibility of the solvent composition is easily lost. On the other hand, when the ratio of HFE (A) exceeds 25 mass %, the solvency with respect to the machining oil, the lubricant, and the like required as a solvent for cleaning or a solvent in the coating film-forming composition is lowered.

In the solvent composition of the present invention, the ratio of HFC (X) is 5 to 25 mass %. When the ratio of HFC (X) is less than 5 mass %, in the use of the solvent composition accompanied by the phase change, the operation of HFC (X) to accelerate the volatilization of tDCE does not function sufficiently, resulting in that the incombustibility of the solvent composition is easily lost. On the other hand, when the ratio of HFC (X) exceeds 25 mass %, the solvency with respect to the machining oil, the lubricant, and the like required as a solvent for cleaning or a solvent in the coating film-forming composition is lowered.

In the solvent composition of the present invention, the ratio of tDCE with respect to the total amount of tDCE and HFE (A) is preferably 75 to 90 mass %. When the ratio of tDCE with respect to the total amount of tDCE and HFE (A) is 75 mass % or more, the solvent composition exhibits sufficiently high solvency with respect to the machining oil, the lubricant, and the like. On the other hand, the ratio is set to 90 mass % or less from a viewpoint of imparting sufficient incombustibility to the solvent composition.

Further, in the solvent composition of the present invention, it is preferable that the ratio of tDCE is 65 to 78 mass %, the ratio of HFE (A) is 5 to 24 mass %, and the ratio of HFC (X) is 5 to 24 mass %, and it is particularly preferable that the ratio of tDCE is 68 to 75 mass %, the ratio of HFE (A) is 9 to 22 mass %, and the ratio of HFC (X) is 9 to 22 mass %, from viewpoints that the solvent composition of the present invention does not have the inflammability, causes small change in the tDCE content even in the use accompanied by the phase change, has excellent cleaning performance when used for the application of cleaning, or has excellent solubility of the nonvolatile organic compound when used for the application of dilution coating.

The total content of tDCE, HFE (A), and HFC (X) in the solvent composition of the present invention is preferably 90 to 100 mass %, more preferably 95 to 100 mass %, and particularly preferably 100 mass % with respect to the total amount of the solvent composition.

The solvent composition of the present invention may contain, other than tDCE, HFE (A), and HFC (X), other solvent other than tDCE, HFE (A), and HFC (X) (simply referred to as "other solvent", hereinafter) in a range in which the effect of the present invention is not impaired, and it may further contain various additives other than the solvent.

The other solvent is preferably an organic solvent which is soluble in tDCE and which has no inflammation point, and can be appropriately selected in accordance with various purposes such as enhancement of the solubility and regulation of an evaporation rate. As the other solvent, there can be cited hydrocarbon, alcohol, ketone, ether, ester, chlorocarbon (except tDCE), HFC (except cHFC-447 and HFC-76-13sf), HFE (except HFE (A)), hydrofluoroolefin (referred to as "HFO", hereinafter), chlorofluoroolefin (referred to as "CFO", hereinafter), hydrochlorofluoroolefin (referred to as "HCFO", hereinafter), and so on, which are soluble in tDCE. The other solvent may be one kind or two kinds or more.

A content of the other solvent in the solvent composition of the present invention is preferably 0 to 10 mass %, and more preferably 0 to 5 mass % with respect to the total amount of the solvent composition. The solvent composition of the present invention achieves both of high solubility and maintenance of incombustibility in the use accompanied by the phase change by the aforementioned content ratio of tDCE, HFE (A), and HFC (X), so that it is particularly preferable that the solvent composition of the present invention does not contain the other solvent.

As the various additives other than the solvent in the solvent composition of the present invention, there can be cited a stabilizer, a metal corrosion inhibitor, and the like. As the stabilizer, concretely, there can be cited nitromethane, nitroethane, nitropropane, nitrobenzene, diethylamine, triethylamine, isopropylamine, diisopropylamine, butyl amine, isobutylamine, tert-butylamine, N-methylbenzylamine, diallylamine, N-methylmorpholine, phenol, o-cresol, m-cresol, p-cresol, thymol, p-tert-butylphenol, tert-butylcatechol, catechol, isoeugenol, o-methoxyphenol, 4,4'-dihydroxyphenyl-2,2-propane, isoamyl salicylate, benzyl salicylate, methyl salicylate, 2,6-di-tert-butyl-p-cresol, 2-(2'-hydroxy-5'-methylphenyl) benzotriazole, 2-(2'-hydroxy-3'-tert-butyl-5'-methylphenyl)-5-chlorobenzotriazole, 1,2,3-benzotriazole, 1-[(N,N-bis-2-ethylhexyl) aminomethyl] benzotriazole, 1,2-propylene oxide, 1,2-butylene oxide, 1,4-dioxane, butyl glycidyl ether, phenyl glycidyl ether, and so on. The stabilizer may be one kind or two kinds or more.

A content of each of the various additives other than the solvent in the solvent composition of the present invention is preferably 0 to 5 mass %, and more preferably 0 to 1 mass % with respect to the total amount of the solvent composition. The total content of the other solvent and the various additives is preferably 10 mass % or less, and more preferably 1 mass % or less with respect to the total amount of the solvent composition, and it is still more preferable that the other solvent and the various additives are not contained.

The solvent composition of the present invention is a solvent composition which exerts no adverse effect on the global environment, has high solubility with respect to the nonvolatile organic compound such as the machining oil, has the incombustibility, and can maintain the initial incombustibility even in the use accompanied by the phase change, and the solvent composition is preferably used for the application of cleaning such as degreasing cleaning, flux cleaning, precision cleaning, and dry cleaning. In addition, the solvent composition of the present invention can be used for the application in which a coating film-forming composition is produced by dissolving a lubricant such as a silicone-based lubricant or a fluorine-based lubricant, an antirust made of a mineral oil, a synthetic oil, or the like, a moisture-proof coating agent for conducting water repellent treatment, an antifouling coating agent such as a fingerprint preventing agent for conducting antifouling treatment, or the like, and a coating film is formed by applying the coating film-forming composition on an article surface.

The articles to which the solvent composition of the present invention is applicable can be widely used for electronic components such as a capacitor, a diode, a transistor, and a SAW filter each being a fundamental element for constituting an electronic circuit, a substrate or a device on which these are mounted, optical components such as a lens and a polarizing plate, automotive parts such as a fuel injection needle to be used for an engine unit and a gear of a drive unit in an automobile, parts of a drive unit to be used for an industrial robot, machine parts such as exterior parts, a carbide tool to be used for a machine tool such as a cutting tool, and the like. Moreover, as materials to which the solvent composition of the present invention can be applied, a wide range of materials such as metal, plastic, elastomer, glass, ceramics, and fabric can be cited, and among them, the solvent composition is suitable for metals such as iron, copper, nickel, gold, silver, and platinum, a sintered metal, glass, a fluorocarbon resin, and engineering plastic such as PEEK.

[Cleaning Method]

A cleaning method of the present invention is a method of cleaning extraneous matter adhering to an article to be cleaned by using the solvent composition of the present invention described above, and is characterized in that the solvent composition of the present invention and the article to be cleaned are brought into contact with each other.

In the cleaning method of the present invention, as the extraneous matter to be removed by cleaning, there can be cited flux, machining oils such as a cutting oil, a quenching oil, a rolling oil, a lubricant, a machine oil, a presswork oil, a stamping oil, a drawing oil, an assembly oil, and a wire drawing oil, a release agent, dust, and the like adhering to various articles to be cleaned. This solvent composition is more excellent in solubility of the machining oil when compared to HFC, HFE and the like being conventional solvent compositions, so that it is preferably used for cleaning of the machining oil.

Further, the solvent composition of the present invention is characterized in that it has high cleaning power, and can remove an asphalt component called as pitch which cannot be removed by HCFCs being the conventional cleaning agents.

Further, the solvent composition of the present invention is applicable to cleaning of the articles to be cleaned made of various materials such as metal, plastic, elastomer, glass, ceramics, and composite materials of these. Besides, the solvent composition of the present invention can be used for cleaning for removing stain of various pieces of clothing formed of fabrics made of natural fiber and made of synthetic fiber.

The cleaning method of the article to be cleaned using the solvent composition of the present invention is not particularly limited except that the solvent composition of the present invention and the article to be cleaned are brought into contact with each other. For example, manual cleaning, immersion cleaning, spray cleaning, immersion-oscillation cleaning, immersion ultrasonic cleaning, steam cleaning, methods by combining these, and the like may be employed. Cleaning conditions such as time and the number of times of the contact, and a temperature of the solvent composition of the present invention at that time, and a cleaning apparatus can be appropriately selected.

The cleaning method of the present invention is preferably a cleaning method having a solvent contact step in which the article to be cleaned is brought into contact with the solvent composition of the present invention in a liquid phase, and a steam contact step in which, after the solvent contact step, the article to be cleaned is exposed to steam generated by evaporating an incombustible solvent composition for steam generation containing tDCE, HFE (A), and HFC (X) (referred to as "solvent composition (V)", hereinafter).

The solvent composition (V) can be set to a solvent composition similar to the solvent composition of the present invention except that the range of the ratios of tDCE, HFE (A), and HFC (X) with respect to the total amount of tDCE, HFE (A), and HFC (X) is different. The solvent composition (V) is preferably the solvent composition of the present invention (the ratio of tDCE, the ratio of HFE (A), and the ratio of HFC (X) with respect to the total amount of tDCE, HFE (A), and HFC (X) are 65 to 80 mass %, 5 to 25 mass %, and 5 to 25 mass %, respectively).

FIG. 1 is a view schematically illustrating one example of a cleaning apparatus which carries out the cleaning method of the present invention having the above-described solvent contact step and steam contact step. The above-described cleaning method will be described below by citing a case of using the cleaning apparatus illustrated in FIG. 1 as an example.

A cleaning apparatus 10 illustrated in FIG. 1 is a three-tank ultrasonic cleaning apparatus that is used mainly for cleaning electronic and electrical components, precision machinery components, optical instrument components, and the like. The cleaning apparatus 10 includes a cleaning tank 1, a rinse tank 2, and a steam generation tank 3 in which solvent compositions La, Lb and Lc are housed, respectively. The cleaning apparatus 10 further includes, above these tanks, a steam zone 4 which is filled with steam generated from the solvent compositions La, Lb and Lc, cooling tubes 9 which cool the steam, and a water separation tank 5 for subjecting a solvent composition Lm obtained by being condensed by the cooling tubes 9 and water adhering to the cooling tubes to a stationary separation. In actual cleaning, an article to be cleaned D is put in a dedicated jig, basket, or the like, and the cleaning is completed while moving the article to be cleaned D in the order of the inside of the solvent composition La housed in the cleaning tank 1, the inside of the solvent composition Lb housed in the rinse tank 2, and a steam zone 43 right above the steam generation tank 3 in the cleaning apparatus 10.

In such a cleaning apparatus, the solvent composition of the present invention is used as at least the solvent composition La housed in the cleaning tank 1 and the solvent composition Lb housed in the rinse tank 2. The solvent composition Lc housed in the steam generation tank 3 is the solvent composition (V), and it is preferably the solvent composition of the present invention.

A heater 7 and an ultrasonic vibrator 8 are provided at a lower portion of the cleaning tank 1. In the cleaning tank 1, a temperature of the solvent composition La is increased by heating with the heater 7, physical force is imparted to the article to be cleaned D by cavitation generated by the ultrasonic vibrator 8 while controlling the temperature to a constant temperature, and stain adhering to the article to be cleaned D is removed by cleaning. As the physical force at this time, other than an ultrasonic wave, any method which has been employed for previous cleaning machines, such as oscillation or a submerged jet of the solvent composition La, may be used. Note that in the cleaning of the article to be cleaned D in the cleaning tank 1, the ultrasonic vibration is not essential, and the cleaning may be performed without the ultrasonic vibration according to need. Further, it is preferable to set the temperature of the solvent composition La in the cleaning tank 1 to 25° C. or more and less than a boiling point of the solvent composition La. When the temperature of the solvent composition La is within the above-described range, it is possible to easily perform the degreasing cleaning of the machining oil and the like, and the cleaning effect because of an ultrasonic wave is high.

When the article to be cleaned D is moved from the cleaning tank 1 to the rinse tank 2 in the cleaning apparatus 10, components of the solvent composition La adhere to a surface to be cleaned. For this reason, it becomes possible to move the article to be cleaned D to the rinse tank 2 while preventing stain components from sticking to the surface of the article to be cleaned D due to drying.

In the rinse tank 2, by immersing the article to be cleaned D in the solvent composition Lb, stain components adhering to the article to be cleaned D in a state of dissolving in the solvent composition La are removed. The rinse tank 2 may have a unit which imparts physical force to the article to be cleaned D, similarly to the cleaning tank 1. The cleaning apparatus 10 has a design in which an overflow of the solvent composition Lb housed in the rinse tank 2 flows into the cleaning tank 1. Further, the cleaning tank 1 includes a pipe 11 which feeds the solvent composition La to the steam generation tank 3 in order to prevent a solution level from becoming equal to or more than a predetermined height.

At a lower portion of the steam generation tank 3, a heater 6 which heats the solvent composition Lc in the steam generation tank 3 is provided. The solvent composition Lc housed in the steam generation tank 3 is boiled by heating with the heater 6, a part or the whole of its composition becomes steam to rise upward as indicated by arrow marks 13, and the steam zone 43 filled with the steam V is formed right above the steam generation tank 3. The article to be cleaned D after being subjected to the cleaning in the rinse tank 2 is transported to the steam zone 43, and exposed to the steam V to be cleaned by the steam (steam contact step). In the steam cleaning, components formed when the steam V is aggregated to be liquefied on a surface of the article to be cleaned D perform cleaning on the article to be cleaned D. The steam V does not contain stain components at all, so that it is effective as the last finish cleaning in the cleaning step. Note that the steam V does not necessarily formed of only the steam generated from the solvent composition Lc, and such a mode is also included in the steam contact step in the cleaning method of the present invention.

Further, in the cleaning apparatus 10, an upper space of the respective tanks is used in common as the steam zone 4. The steam generated from the cleaning tank 1, the rinse tank 2, and the steam generation tank 3 is recovered from the steam zone 4 as the solvent composition Lm by being cooled and condensed by the cooling tubes 9 provided at an upper portion of a wall surface of the cleaning apparatus 10. The aggregated solvent composition Lm is then housed in the water separation tank 5 via a pipe 14 connecting the cooling tubes 9 and the water separation tank 5. In the water separation tank 5, water mixing in the solvent composition Lm is separated. The solvent composition Lm from which the water is separated is returned to the rinse tank 2 through a pipe 12 connecting the water separation tank 5 and the rinse tank 2. In the cleaning apparatus 10, such a mechanism allows a reduction in an evaporation loss of the solvent composition.

Furthermore, in order to increase a cleaning effect, a cooling device is placed in the rinse tank 2, which allows a temperature of the solvent composition Lb in the rinse tank 2 to be maintained at a low temperature and a temperature of the immersed article to be cleaned D to be kept low, and it is thereby effective to make a temperature difference between the steam temperature and the temperature of the article to be cleaned D large and to increase a condensed amount of the steam V at the surface of the article to be cleaned D. Concretely, it is preferable to set the temperature of the solvent composition Lb in the rinse tank 2 to 10 to 45° C. Further, the temperature of the solvent composition La in the cleaning tank 1 is preferably higher than the temperature of the solvent composition Lb in the rinse tank 2 in terms of cleaning performance.

In the cleaning apparatus 10, by circulating the solvent compositions La, Lb and Lc housed in the respective tanks while changing their states into a liquid or a gas in a manner as described above, the stain components brought into the rinse tank 2 are accumulated continuously in the steam generation tank 3, and it becomes possible to maintain cleanliness of the rinse tank 2 and to perform the steam cleaning in the steam zone 43.

When the article to be cleaned is cleaned by using the cleaning apparatus 10 in this embodiment, by putting the solvent composition of the present invention in the cleaning tank 1, the rinse tank 2, and the steam generation tank 3 as the solvent compositions La, Lb and Lc, at a time of stating the operation, for example, it is possible to make the solvent composition Lc satisfy the composition range of the solvent composition (V) in a state where the solvent composition La and the solvent composition Lb maintain the composition range of the solvent composition of the present invention, when the cleaning reaches a steady state.

Specifically, when the solvent composition of the present invention in the above-described cleaning method is set to a solvent composition L, a composition of the solvent composition L which is put at a time of starting the operation of the cleaning apparatus 10 changes in each of the cleaning tank 1, the rinse tank 2, the steam generation tank 3, the steam zone 4, and the water separation tank 5, in accordance with the operation of the cleaning apparatus 10, and then the composition becomes steady. The solvent compositions La and Lb in the steady state housed in the cleaning tank 1 and the rinse tank 2, respectively, are within the range of the solvent composition of the present invention having high solubility and an incombustible composition, although their compositions slightly change when compared to the solvent composition L. When compared to the solvent composition L, the composition of the solvent composition Lc housed in the steam generation tank 3 is different, and the solvent composition Lc is sometimes out of the range of the solvent composition of the present invention. Even in such a case, the content ratio of tDCE is low, the composition is within the composition range of the solvent composition (V), and the incombustible composition is secured. Further, it is possible to stably perform a continuous operation in this steady state while securing high cleaning power and safety.

Note that the cleaning method having the solvent contact step and the steam contact step in the cleaning method of the present invention is not limited to the above-described embodiment, and this embodiment can be changed or modified without departing from the spirit and the scope of the present invention. For example, the solvent contact step may be performed only once, it is preferably repeated two times or more, and it is more preferably repeated two to three times. Further, a tank in which a condensate obtained by condensing the steam in the steam zone is returned, may be a tank other than the rinse tank 2, and furthermore, there is no need to reuse the condensate.

By using the solvent composition of the present invention, the cleaning method of the present invention is a cleaning method having high cleaning performance, exerting no adverse effect on the global environment, and having secured safety even in the use accompanied by the phase change. Further, an article cleaned by the solvent composition of the present invention has a characteristic such that cleaning failure is unlikely to occur since no residue of the machining oil or the like is observed on a surface of the article, and thus a surface state after finishing is good.

[Coating Film-Forming Composition and Method of Forming a Coating Film]

The solvent composition of the present invention can be used for a solvent for dilution coating of a nonvolatile organic compound. Specifically, the coating film-forming composition of the present invention is characterized in that it contains the solvent composition of the present invention and the nonvolatile organic compound. Further, a method of forming a coating film of the present invention is characterized in that the above-described coating film-forming composition is applied on an article to be coated, and then the solvent composition is evaporated to form a coating film made of the above-described nonvolatile organic compound.

Here, the nonvolatile organic compound in the present invention indicates one which has a boiling point higher than that of the solvent composition of the present invention, and in which the organic compound still remains on a surface even after evaporation of the solvent composition. As the nonvolatile organic compounds, concretely, there can be cited a lubricant for imparting lubricity to an article, an antirust for imparting an anti-rust effect to metal parts, a moisture-proof coating agent for imparting water repellency to an article, an antifouling coating agent such as a fingerprint preventing agent for imparting antifouling ability to an article, and the like. In the coating film-forming composition and the method of forming the coating film of the present invention, it is preferable to use the lubricant as the nonvolatile organic compound from a viewpoint of solubility.

The lubricant means one which is used for reducing friction on a contact surface and preventing generation of heat and abrasion damage when two members move in a state where their surfaces are brought into contact with each other. The lubricant may be any form of liquid (oil), semi-solid (grease), and solid.

As the lubricant, in terms of high solubility to tDCE, a fluorine-based lubricant or a silicone-based lubricant is preferable. Note that the fluorine-based lubricant means a lubricant having a fluorine atom in a molecule. Further, the silicone-based lubricant means a lubricant containing silicone.

The lubricant contained in the coating film-forming composition may be one kind or two kinds or more. Each of the fluorine-based lubricant and the silicone-based lubricant may be used alone, or they may be used in combination.

As the fluorine-based lubricant, there can be cited a fluorine oil, fluorine grease, or a fluorine-based solid lubricant such as resin powder of polytetrafluoroethylene. As the fluorine oil, a low polymer of perfluoropolyether or chlorotrifluoroethylene is preferable. As commercial products of the fluorine oil, for example, there can be cited product names "Krytox (registered trademark) GPL102" (manufactured by Du Pont Co., Ltd.), "DAIFLOIL #1", "DAIFLOIL #3", "DAIFLOIL #10", "DAIFLOIL #20", "DAIFLOIL #50", "DAIFLOIL #100", "DEMNUM S-65" (these are manufactured by Daikin Industries, Ltd.), and the like.

As the fluorine grease, one in which the fluorine oil such as the low polymer of perfluoropolyether or chlorotrifluoroethylene is used as a base oil and powder of polytetrafluoroethylene or other thickeners are compounded is preferable. As commercial products of the fluorine grease, for example, there can be cited product names "Krytox (registered trademark) grease 240AC" (manufactured by Du Pont Co., Ltd.), "DAIFLOIL grease DG-203", "DEMNUM L65", "DEMNUM L100", "DEMNUM L200" (these are manufactured by Daikin, Ltd.), "Sumitec F936" (manufactured by SUMICO LUBRICANT CO., LTD.), "Molykote (registered trademark) HP-300", "Molykote (registered trademark) HP-500", "Molykote (registered trademark) HP-870", "Molykote (registered trademark) 6169" (these are manufactured by Dow Corning Toray Co., Ltd.), and the like.

As the silicone-based lubricant, a silicone oil or silicone grease can be cited. As the silicone oils, a dimethyl silicone, a methyl hydrogen silicone, a methyl phenyl silicone, a cyclic dimethyl silicone, an amine group-modified silicone, a diamine group-modified silicone, and a modified silicone oil in which an organic group is introduced into a side chain or a terminal are preferable. As commercial products of the silicone oil, for example, there can be cited product names "Shin-Etsu Silicone KF-96", "Shin-Etsu Silicone KF-965", "Shin-Etsu Silicone KF-968", "Shin-Etsu Silicone KF-99", "Shin-Etsu Silicone KF-50", "Shin-Etsu Silicone KF-54", "Shin-Etsu Silicone HIVAC F-4", "Shin-Etsu Silicone HIVAC F-5", "Shin-Etsu Silicone KF-56A", "Shin-Etsu Silicone KF-995", "Shin-Etsu Silicone KF-868", "Shin-Etsu Silicone KF-859" (these are manufactured by Shin-Etsu Chemical Co., Ltd.), "SH200" (manufactured by Dow Corning Toray Co., Ltd.), and the like.

As the silicone grease, products in which the various silicone oils cited above are used as a base oil and a thickener such as metal soap or various additives are compounded are preferable. As commercial products of the silicone grease, for example, there can be cited product names "Shin-Etsu Silicone G-30 Series", "Shin-Etsu Silicone G-40 Series", "Shin-Etsu Silicone FG-720 Series", "Shin-Etsu Silicone G-411", "Shin-Etsu Silicone G-501", "Shin-Etsu Silicone G-6500", "Shin-Etsu Silicone G-330", "Shin-Etsu Silicone G-340", "Shin-Etsu Silicone G-350", "Shin-Etsu Silicone G-630" (these are manufactured by Shin-Etsu Chemical Co., Ltd.), "Molykote (registered trademark) SH33L", "Molykote (registered trademark) 41", "Molykote (registered trademark) 44", "Molykote (registered trademark) 822M", "Molykote (registered trademark) 111", "Molykote (registered trademark) grease for high vacuum", "Molykote (registered trademark) heat diffusion compound" (these are manufactured by Dow Corning Toray Co., Ltd.), and the like.

Further, as one which can be exemplified as the fluorine-based lubricant and as the silicone-based lubricant, there can be cited a fluorosilicone oil which is a modified silicone oil in which a fluoroalkyl group is substituted for a terminal or a side chain. As commercial products of the fluorosilicone oil, for example, there can be cited product names "Unidyne (registered trademark) TG-5601" (manufactured by Daikin Industries, Ltd.), "Molykote (registered trademark) 3451", "Molykote (registered trademark) 3452" (these are manufactured by Dow Corning Toray Co., Ltd.), "Shin-Etsu Silicone FL-5", "Shin-Etsu Silicone X-22-821", "Shin-Etsu Silicone X-22-822", "Shin-Etsu Silicone FL-100" (these are manufactured by Shin-Etsu Chemical Co., Ltd.), and the like.

These lubricants can be used as a coating film for, for example, industrial equipment, tray parts for a CD and a DVD in a personal computer and an audiovisual apparatus, household appliances and office equipment such as a printer, a copier, and a flux device, and the like for which the fluorine-based lubricant is used normally as the coating film. Further, for example, they can be used for a needle and a cylinder of a syringe, medical tube parts, a metal blade, a catheter, and the like for which the silicone-based lubricant is used normally as the coating film.

The antirust means one which is used for preventing rust of metal materials by covering a surface of metals which are easily oxidized by oxygen in the air to generate rust and blocking oxygen from the metal surface. As the antirusts, there can be cited a mineral oil, and synthetic oils such as polyol esters, polyalkylene glycols, and polyvinyl ethers.

The moisture-proof coating agent and the antifouling coating agent are ones which are used for imparting a moisture-proof property and an antifouling property to plastic, rubber, metal, glass, a mounted circuit board, and the like. As product examples of the moisture-proof coating agent, there can be cited TOPAS 5013, TOPAS 6013, TOPAS 8007 (manufactured by Polyplastics Co., Ltd.), ZEONOR 1020R, ZEONOR 1060R (manufactured by Zeon Corporation), Apel 6011T, Apel 8008T (manufactured by Mitsui Chemicals, Inc.), SFE-DPO2H, SNF-DP2OH (manufactured by AGC SEIMI CHEMICAL CO., LTD.). As product examples of the antifouling coating agent such as a fingerprint preventing agent, there can be cited OPTOOL DSX, OPTOOL DAC (manufactured by Daikin Industries, Ltd.), Fluoro Surf FG-5000 (manufactured by Fluoro Technology Co., Ltd.), SR-4000A (manufactured by AGC SEIMI CHEMICAL CO., LTD.), and the like.

The coating film-forming composition of the present invention is normally prepared as a composition in solution form in which the nonvolatile organic compound is dissolved in the solvent composition of the present invention. A manufacturing method of the coating film-forming composition is not particularly limited as long as it is a method of allowing the nonvolatile organic compound to be uniformly dissolved in the solvent composition of the present invention in a predetermined ratio. The coating film-forming composition of the present invention is basically constituted of only the nonvolatile organic compound and the solvent composition of the present invention. In the following explanation, the coating film-forming composition using the lubricant as the nonvolatile organic compound is referred to as "lubricant solution". The same applies to coating film-forming compositions using other nonvolatile organic compounds.

A content of the lubricant with respect to a total amount of solution in the lubricant solution (100 mass %) is preferably 0.01 to 50 mass %, more preferably 0.05 to 30 mass %, and still more preferably 0.1 to 20 mass %. The remainder except the lubricant of the lubricant solution is the solvent composition. As long as the content of the lubricant is within the above-described range, a film thickness of a coating film when the lubricant solution is applied and a thickness of a lubricant coating film after drying are easily regulated in a proper range.

A content of each of the nonvolatile organic compounds such as the antirust, the moisture-proof coating agent, and the antifouling coating agent with respect to a total amount of each of solutions (coating film-forming compositions) in the coating film-forming compositions such as an antirust solution, a moisture-proof coating agent solution, and an antifouling coating agent solution, is also preferably in the same range as the above-described content of the lubricant in the lubricant solution.

When the coating film-forming composition containing the above-described solvent composition and nonvolatile organic compound is applied on an article to be coated, and the solvent composition is evaporated from the coating film-forming composition applied on the article to be coated, a coating film constituted of the nonvolatile organic compound can be formed on the article to be coated.

As the articles to be coated on which the coating film of the lubricant, the antirust, the moisture-proof coating agent, the antifouling coating agent, or the like is formed, namely, the coating film-forming composition each containing these is applied, articles to be coated made of various materials such as metal, plastic, elastomer, glass, and ceramics can be employed. As concrete articles, the articles explained above for each of the nonvolatile organic compounds can be cited.

As an applying method of the coating film-forming composition, for example, there can be cited applying by using a brush, applying by spraying, applying by immersing the articles in the coating film-forming composition, an applying method in which the coating film-forming composition is brought into contact with an inner wall of a tube or a needle by pumping up the coating film-forming composition, and so on.

As a method of evaporating the solvent composition from the coating film-forming composition, a publicly-known drying method can be cited. As the drying method, for example, air drying, drying by heating, or the like can be cited. A drying temperature is preferably 20 to 100° C.

In the coating film-forming composition and the method of forming the coating film using the same of the present invention described above, the solvent composition of the present invention is used as a dilution coating solvent of the nonvolatile organic compound, so that no adverse effect is exerted on the global environment. Further, the solvent composition of the present invention has a high content of tDCE, so that it is excellent in the solubility of the nonvolatile organic compound, there is no chance that it becomes cloudy or the nonvolatile organic compound is separated during storage, and it is possible to form a uniform coating film. Besides, the solvent composition of the present invention does not form a composition having an inflammation point in accordance with the gas-liquid phase change, and thus it is safe even if the solvent composition is used for forming the coating film.

EXAMPLES

Hereinafter, the present invention will be described in detail by examples. The present invention is not limited to these examples.

Examples 1 to 16; Solvent Composition

The following tDCE, HFE-347pc-f, HFE-467sc-f, cHFC-447, and HFC-76-13sf were mixed in a ratio shown in Tables 1 and 2, to thereby produce solvent compositions of Examples 1 to 16. The Examples 1 to 8, 15 and 16 are examples of the present invention, and the Examples 9 to 14 are comparative examples.
(Manufacturers, Product Names of Compounds)
tDCE; trans-1,2-dichloroethylene (manufactured by AXI-ALL CORPORATION)
HFE-347pc-f; "ASAHIKLIN (registered trademark) AE-3000" (manufactured by Asahi Glass Co., Ltd.)
HFE-467sc-f; manufactured by the method described in JP-A No. H09-263559
cHFC-447; "ZEORORA-H" (manufactured by Zeon Corporation)
HFE-76-13sf; "ASAHIKLIN (registered trademark) AC-6000" (manufactured by Asahi Glass Co., Ltd.)
(Evaluation)

On the solvent compositions obtained in the above-described respective examples, solubility tests with respect to a machining oil and a pitch, an inflammability test, and a cleaning test were performed by the following methods to perform evaluation.
<Solubility Tests (1) to (4)>

As the solubility test (1), 10 g of the solvent composition obtained in each of the Examples was put in a screw tube bottle made of glass, 5 g of a product name "Daphne Magplus HT-10" (manufactured by Idemitsu Kosan Co., Ltd.) being a cutting oil, was added thereto, the bottle was capped and shaken well with hands to perform mixing to prepare a test solution, and the test solution was left still for one minute. Note that the test was carried out under a condition of a temperature of 23° C. The test solution after being left still was visually observed, and as a result of this, a case where cloudiness and two-layer separation were not recognized was evaluated as "A", and a case where the cloudiness or the two-layer separation was recognized was evaluated as "B".

A test was performed similarly to the solubility test (1) except that the cutting oil (the product name "Daphne Magplus HT-10" (manufactured by Idemitsu Kosan Co., Ltd.) was changed to each of the following cutting oils, and the solubility of each of the cutting oils was evaluated based on the same criteria.
Solubility test (2); product name "Daphne Magplus AM20" (manufactured by Idemitsu Kosan Co., Ltd.)
Solubility test (3); product name "Daphne Magplus HM25" (manufactured by Idemitsu Kosan Co., Ltd.)
Solubility test (4); product name "G-6318FK" (manufactured by NIHON KOHSAKUYU CO., LTD.)
<Solubility Test (5)>

As a test piece for a solubility test (5), there was produced a glass substrate test piece with a pitch (asphalt) adhered thereto obtained in a manner that spray pitch (product name "SPRAY PITCH": manufactured by KOKONOE ELECTRIC CO., LTD.) was sprayed on a glass substrate of 10 mm×20 mm×5 mm and dried for one night. The solvent composition obtained in each of the Examples of 100 g was put in a glass beaker of 100 ml, one test piece obtained in the above was immersed for one minute, and a degree of removal of the pitch from the test piece was visually evaluated. A case where the pitch was able to be removed from the glass substrate test piece was evaluated as "A", and a case where the pitch component remained on the glass substrate test piece was evaluated as "B".
<Inflammability Test>

Regarding the solvent composition obtained in each of the Examples of 200 mL, the presence or absence of an inflammation point from 23° C. to a boiling point was checked by using a Cleveland open-cup inflammation point tester (manufactured by YOSHIDA SEISAKUSHO CO., LTD., model 828). Results of the solubility tests (1) to (5) and the inflammability test are shown in lower columns of Tables 1 and 2. Regarding the results of the inflammability test, "P" shows presence, and "A" shows absence in Tables 1 and 2.

TABLE 1

| | Example | | 1 | 2 | 3 | 4 | 5 | 6 | 7 | 8 |
|---|---|---|---|---|---|---|---|---|---|---|
| Composition | | tDCE | 70.0 | 70.0 | 70.0 | 75.0 | 75.0 | 70.0 | 70.0 | 75.0 |
| [mass %] | HFE(A) | HFE-347pc-f | 10.0 | 15.0 | 20.0 | 12.5 | 15.0 | 20.0 | 10.0 | 17.5 |
| | | HFE-467sc-f | | | | | | | | |
| | HFC(X) | cHFC-447 | 20.0 | 15.0 | 10.0 | 12.5 | 10.0 | | | |
| | | HFC-76-13sf | | | | | | 10.0 | 20.0 | 7.5 |
| | | Total | 100 | 100 | 100 | 100 | 100 | 100 | 100 | 100 |
| | tDCE/(tDCE + HFE(A)) × 100 | | 87.5 | 82.4 | 77.8 | 85.7 | 83.3 | 77.8 | 87.5 | 81.1 |
| Physical | Solubility | Test (1) | A | A | A | A | A | A | A | A |
| property/ | | Test (2) | A | A | A | A | A | A | A | A |
| performance | | Test (3) | A | A | A | A | A | A | A | A |
| | | Test (4) | A | A | A | A | A | A | A | A |
| | | Test (5) | A | A | A | A | A | A | A | A |
| | Inflammability | | A | A | A | A | A | A | A | A |

TABLE 2

| Example | | | 9 | 10 | 11 | 12 | 13 | 11 | 15 | 16 |
|---|---|---|---|---|---|---|---|---|---|---|
| Composition [mass %] | | tDCE | 60.0 | 85.0 | 60.0 | 85.0 | 85.0 | 70.0 | 70.0 | 70.0 |
| | HFE(A) | HFE-347pc-f | 20.0 | 5.0 | 20.0 | 5.0 | 15.0 | 30.0 | | |
| | | HFE-467sc-f | | | | | | | 15.0 | 20.0 |
| | HFC(X) | cHFC-447 | 20.0 | 10.0 | | | | | 15.0 | |
| | | HFC-76-13sf | | | 20.0 | 10.0 | | | | 10.0 |
| | | Total | 100 | 100 | 100 | 100 | 100 | 100 | 100 | 100 |
| tDCE/(tDCE + HFE(A)) × 100 | | | 75.0 | 94.4 | 75.0 | 94.4 | 85.0 | 70.0 | 82.4 | 77.8 |
| Physical property/ performance | Solubility | Test (1) | B | A | B | A | A | A | A | A |
| | | Test (2) | B | A | B | A | A | A | A | A |
| | | Test (3) | B | A | B | A | A | A | A | A |
| | | Test (4) | B | A | B | A | A | A | A | A |
| | | Test (5) | B | A | B | A | A | A | A | A |
| | Inflammability | | A | P | A | P | P | A | A | A |

Cleaning Test; Examples 17 to 31

The solvent composition obtained in each of the above-described Examples 1 to 12 and 14 to 16 was applied to a cleaning apparatus similar to that illustrated in FIG. 1 to perform a cleaning test. Note that this cleaning test is an evaluation test of each of the above-described solvent compositions, and is also an example of the cleaning method of the present invention. Examples 17 to 24, 30 and 31 are examples of the present invention, and Examples 25 to 29 are comparative examples.

For all of three tanks of the cleaning tank 1 (capacity: 5.2 liters), the rinse tank 2 (capacity: 5.0 liters), and the steam generation tank 3 (capacity: 2.8 liters) of the cleaning apparatus 10, the solvent composition obtained in the above-described Example 1 was prepared. After that, a continuous operation was performed for 8 hours without conducting cleaning, and a composition of the solvent in each tank in the cleaning apparatus 10 was stabilized to create a steady state. Further, as the article to be cleaned D, there was prepared a test piece obtained by immersing a small piece (25 mm×30 mm×2 mm) of SUS-304 in a cutting oil similar to that used in the solubility test (1).

By using the cleaning apparatus 10 in the steady state, the test piece was moved in the order of the cleaning tank 1, the rinse tank 2, and the steam zone 43 right above the steam generation tank 3 to be cleaned, as illustrated in FIG. 1. At that time, a temperature of the solvent composition La in the cleaning tank 1 was set to 35° C., and in the cleaning in the cleaning tank 1, an ultrasonic wave with a frequency of 40 kHz and an output of 200 W was generated for one minute. Further, a temperature of the solvent composition Lb in the rinse tank 2 was set to 25° C., and the solvent composition Lc in the steam generation tank 3 was heated so as to be in a boiled state all the time. During the cleaning, the solvent composition Lm obtained by aggregating the steam in the steam zone 4 and removing water was returned to the rinse tank 2, an overflow from the rinse tank 2 was made to flow into the cleaning tank 1, and besides, an excessive solvent composition La in the cleaning tank 1 was fed to the steam generation tank 3.

After the termination of the cleaning, the solvent composition La in the cleaning tank 1 and the solvent composition Lc in the steam generation tank 3 were collected, and chemical compositions of the collected compositions were analyzed through gas chromatography (GC7890, manufactured by Agilent Technologies, Inc.), and the inflammability of each of the collected compositions was evaluated similarly to the above-described inflammability test.

Further, a remaining state of the cutting oil at the cleaned test piece was visually observed to evaluate the cleaning performance. Note that a case where almost all of the cutting oil was removed was evaluated as "A", and a case where the cutting oil remained considerably was evaluated as "B".

Each of the solvent compositions obtained in the above-described Examples 2 to 12 and 14 to 16 was also subjected to a cleaning test similarly to the case of the solvent composition of the Example 1 described above, thereby evaluating the cleaning performance and the inflammability of the solvent composition in each tank in the steady state.

Table 3 shows evaluation results of the cleaning performance together with example numbers and compositions of the solvent compositions prepared at the time of starting the operation of the cleaning apparatus 10, and the compositions and the inflammability of the solvent composition La in the cleaning tank 1 and the solvent composition Lc in the steam generation tank 3 after the operation became steady. Note that in Table 3, the composition [mass %] indicates mass % of each component in the total amount of the composition in the order of tDCE/HFE (A)/HFC (X). HFE (A) is HFE-347pc-f or HFE-467sc-f, and HFC (X) is cHFC-447 or HFC-76-13sf, which are as shown in Tables 1 and 2 for each solvent composition of each Example number. The composition [mass %] of the solvent composition of the Example 29 indicates mass % of tDCE/HFE-347pc-f.

TABLE 3

| | | When performing preparation Solvent composition | Steady state (after operation of 8 hours) | | | | |
|---|---|---|---|---|---|---|---|
| | | | Solvent composition La in cleaning tank | | Solvent composition Lc in steam generation tank | | |
| Example | Example Number | Composition [mass %] | Composition [mass %] | Inflammability | Composition [mass %] | Inflammability | Cleaning performance |
| 17 | 1 | 70/10/20 | 70.3/10.5/19.2 | Absence | 68.8/7.6/23.6 | Absence | A |
| 18 | 2 | 70/15/15 | 69.9/16.7/13.4 | Absence | 70.5/9.5/20 | Absence | A |
| 19 | 3 | 70/20/10 | 69.8/20.4/9.8 | Absence | 71.3/17.7/11 | Absence | A |

TABLE 3-continued

| | | When performing preparation Solvent composition | Steady state (after operation of 8 hours) | | | | |
|---|---|---|---|---|---|---|---|
| | | | Solvent composition La in cleaning tank | | Solvent composition Lc in steam generation tank | | |
| Example | Example Number | Composition [mass %] | Composition [mass %] | Inflammability | Composition [mass %] | Inflammability | Cleaning performance |
| 20 | 4 | 75/12.5/12.5 | 75/13.2/11.8 | Absence | 75.4/8.7/15.9 | Absence | A |
| 21 | 5 | 75/15/10 | 74.7/16.2/9.1 | Absence | 77.1/10.1/12.8 | Absence | A |
| 22 | 6 | 70/20/10 | 69.9/22.9/7.2 | Absence | 70.6/8.8/20.6 | Absence | A |
| 23 | 7 | 70/10/20 | 73.1/12.4/14.5 | Absence | 58.4/5.3/36.3 | Absence | A |
| 24 | 8 | 75/17.5/7.5 | 74.8/19.6/5.6 | Absence | 75.2/10.4/14.4 | Absence | A |
| 25 | 9 | 60/20/20 | 59.9/20.4/19.7 | Absence | 61.6/16.4/22 | Absence | B |
| 26 | 10 | 85/5/10 | 85.5/5.1/9.4 | Presence | 84.6/4.2/11.2 | Presence | A |
| 27 | 11 | 60/20/20 | 61.3/22.3/16.4 | Absence | 57.8/12.8/29.4 | Absence | B |
| 28 | 12 | 85/5/10 | 84.3/6.9/8.8 | Presence | 85.4/2.2/12.4 | Presence | A |
| 29 | 14 | 70/30 | 65/35 | Absence | 84.3/15.7 | Presence | A |
| 30 | 15 | 70/15/15 | 73.4/16.6/10.0 | Absence | 58.2/9.4/32.4 | Absence | A |
| 31 | 16 | 70/20/10 | 73.2/21.4/5.4 | Absence | 58/14.5/27.5 | Absence | A |

As can be seen from Tables 1 and 2, in each of the solvent compositions of the examples 1 to 8, 15 and 16 that fall within the composition range of the solvent composition of the present invention, excellent solubility of the cutting oil was provided, and no inflammation point was observed. Further, as shown in Table 3, in the cleaning method in which the solvent composition is accompanied by the phase change, concretely, the cleaning method having the solvent contact step and the steam contact step using the cleaning apparatus 10, the Examples 17 to 24, 30 and 31 as the cleaning methods of the present invention using the solvent compositions of the Examples 1 to 8, 15 and 16 that fall within the composition range of the solvent composition of the present invention exhibited the cleaning performance by maintaining the composition of the solvent composition La in the cleaning tank 1 to the composition range of the solvent composition of the present invention, and enabled stable operation while preventing the composition of the solvent composition in each tank from becoming the inflammable composition.

The Examples 9 to 13 being out of the composition range of the solvent composition of the present invention had good solubility but had an inflammation point, or when they had no inflammation point, they had insufficient solubility (Table 1). Further, as can be seen from Table 3, in the Examples 25 to 28 which were out of the category of the cleaning method of the present invention and used the solvent compositions of the Examples 9 to 12 being out of the composition range of the solvent composition of the present invention, the evaluation result of either the cleaning performance or the inflammability was not sufficient in the cleaning method in which the solvent composition is accompanied by the phase change. It was clarified that the cleaning method of the Example 29 (the case of using the solvent composition of the Example 14) had the cleaning performance, and even if the composition when performing preparation was not the inflammable composition, the solvent composition Lc having the inflammable composition was formed in the steam generation tank 3 during the operation of the cleaning apparatus 10.

Examples 32 to 38; Coating Film-Forming Composition

By using the solvent compositions obtained in the above-described Examples 2, 4, 6 and 15, coating film-forming compositions of Examples 32 to 38 (as examples of the present invention) were produced and evaluated in the following manner.

The solvent composition obtained in the Example 2 and a product name "Krytox (registered trademark) GPL102" (a fluorine-based oil, manufactured by Du Pont Co., Ltd.) being a fluorine-based lubricant were mixed, to prepare a lubricant solution in which a content of the lubricant was 0.5 mass % with respect to the total amount of the lubricant solution. Further, by using "Shin-Etsu Silicone KF-96" (a silicone oil, manufactured by Shin-Etsu Chemical Co., Ltd.) being a silicone-based lubricant in place of the fluorine-based lubricant, a lubricant solution was prepared similarly to the above.

In a similar manner to the above except that the solvent composition in the Example 2 was changed to the solvent compositions in the Examples 4, 6, there were prepared two kinds of lubricant solutions in each of which, with respect to each solvent composition, each of the fluorine-based lubricant and the silicone-based lubricant was contained in a ratio shown in Table 4, relative to the total amount of the lubricant solution. Regarding a solvent composition in the Example 15, only a lubricant solution of a fluorine-based lubricant was prepared similarly to the above.

(Evaluation)

Regarding the lubricant solutions obtained in the above-described respective Examples, the solubility, the drying property at the time of forming the coating film, and the uniformity of the obtained coating film were evaluated.

<Solubility>

The lubricant solution in each of the Examples obtained above was visually observed to evaluate a dissolved state of the lubricant. The evaluation of the solubility was carried out under a condition of a temperature of 23° C. A case where cloudiness and two-layer separation were not recognized in the lubricant solution was evaluated as "A", and a case where the cloudiness or the two-layer separation was recognized was evaluated as "B".

<Drying Property, Uniformity of Coating Film>

On a surface of an aluminum-evaporated plate being a plate made of iron on which aluminum was evaporated, the lubricant solution obtained in each of the above-described Examples was applied to have a thickness of 0.4 mm, and air-dried under a condition of 19 to 21° C., to thereby form a lubricant coating film on the surface of the aluminum-evaporated plate. A state of the obtained lubricant coating film was visually observed, and a case where a uniform coating film was recognized to be formed without non-uniformity and defect was evaluated as "A", and a case where the non-uniformity or the defect was recognized was evaluated as "B". Further, the drying property of the lubricant solution at the time of forming the lubricant coating film was visually observed, and a case where the solvent was immediately dried was evaluated as "A", and a case where the solvent was not dried was evaluated as "B". The evaluation results are shown in Table 4 together with the compositions of the lubricant solutions.

TABLE 4

| Example | | 32 | 33 | 34 | 35 | 36 | 37 | 38 |
|---|---|---|---|---|---|---|---|---|
| Solvent composition Example Number | | 2 | 2 | 4 | 4 | 6 | 6 | 15 |
| Composition [mass %] | Solvent composition | 99.5 | 99.5 | 99.5 | 99.5 | 99.5 | 99.5 | 99.5 |
| | GPL102 | 0.5 | | 0.5 | | 0.5 | | 0.5 |
| | KF-96 | | 0.5 | | 0.5 | | 0.5 | |
| | Total | 100 | 100 | 100 | 100 | 100 | 100 | 100 |
| Performance | Solubility | A | A | A | A | A | A | A |
| | Drying property | A | A | A | A | A | A | A |
| | Uniformity of coating film | A | A | A | A | A | A | A |

As can be seen from Table 4, each of the Examples (Examples 32 to 38) of the coating film-forming compositions using the solvent compositions of the Examples 2, 4, 6 and 15 that fall within the composition range of the solvent composition of the present invention has excellent solubility of the lubricant, forms a uniform coating film, and has excellent drying property.

What is claimed is:

1. A solvent composition, comprising:
   trans-1,2-dichloroethylene;
   at least one hydrofluoroether (A) selected from the group consisting of 1,1-difluoroethyl-2,2,2-trifluoroethyl ether, 1,1,2,2-tetrafluoroethyl-2,2,2-trifluoroethyl ether, and 1,1-difluoroethyl-2,2,3,3,3-pentafluoropropyl ether; and
   at least one hydrofluorocarbon (X) selected from the group consisting of 1,1,2,2,3,3,4-heptafluorocyclopentane[H] and 1,1,1,2,2,3,3,4,4,5,5,6,6-tridecafluorohexane,
   wherein a ratio of the trans-1,2-dichloroethylene to a total amount of the trans-1,2-dichloroethylene, the hydrofluoroether (A), and the hydrofluorocarbon (X) is in a range of 65 to 80 mass %,
   wherein a ratio of the hydrofluoroether (A) to the total amount is in a range of 5 to 25 mass %, and
   wherein a ratio of the hydrofluorocarbon (X) to the total amount is in a range of 5 to 25 mass %.

2. The solvent composition of claim 1, wherein a ratio of the trans-1,2-dichloroethylene to a total amount of the trans-1,2-dichloroethylene and the hydrofluoroether (A) is in a range of 75 to 90 mass %.

3. The solvent composition of claim 1, wherein a ratio of the total amount of the trans-1,2-dichloroethylene, the hydrofluoroether (A), and the hydrofluorocarbon (X) to a total amount of the solvent composition is in a range of 90 to 100 mass %.

4. The solvent composition of claim 1, wherein the hydrofluoroether (A) is 1,1,2,2-tetrafluoroethyl-2,2,2-trifluoroethyl ether.

5. The solvent composition of claim 1, wherein the hydrofluorocarbon (X) is 1,1,2,2,3,3,4-heptafluorocyclopentane.

6. A method of cleaning, comprising: contacting an article to be cleaned with the solvent composition of claim 1.

7. A coating film-forming composition, comprising: the solvent composition of claim 1 and a nonvolatile organic compound.

8. The coating film-forming composition of claim 7, wherein the nonvolatile organic compound is a lubricant.

9. The coating film-forming composition of claim 8, wherein the lubricant is at least one selected from the group consisting of a silicone-based lubricant and a fluorine-based lubricant.

10. A method of forming a coating film, comprising:
    applying the coating film-forming composition of claim 7 to an article to be coated; and
    evaporating the coating film-forming composition to form a coating film comprising the nonvolatile organic compound.

11. The solvent composition of claim 2, wherein a ratio of the total amount of the trans-1,2-dichloroethylene, the hydrofluoroether (A), and the hydrofluorocarbon (X) to a total amount of the solvent composition is in a range of 90 to 100 mass %.

* * * * *